United States Patent [19]

Drulias et al.

[11] Patent Number: 5,179,942
[45] Date of Patent: Jan. 19, 1993

[54] LUMBAR SUPPORT THERAPEUTIC HEAT/COOLING/AIR PILLOW BELT

[76] Inventors: Dean J. Drulias, 2024 MacArthur St., Rancho Palos Verde, Calif. 90732; Kevin P. Barry, 22 Sea Bridge, Laguna Niguel, Calif. 92677

[21] Appl. No.: 808,905

[22] Filed: Dec. 17, 1991

[51] Int. Cl.⁵ ............................................. A61F 5/32
[52] U.S. Cl. ................... 128/101.1; 128/402; 128/106.1; 602/2; 602/19
[58] Field of Search ............. 128/384, 402, 82.1, 128/68.1, 100.1, 101.1, 105.4, 106.1, 107.1, 111.1, 95.1, 112.1; 602/19, 2

[56] References Cited

U.S. PATENT DOCUMENTS

| | | | |
|---|---|---|---|
| 1,908,906 | 5/1933 | Loeb | 128/95.1 |
| 3,013,561 | 12/1961 | Nelkin | 128/101.1 |
| 3,096,760 | 7/1963 | Nelkin | 128/95.1 |
| 3,141,457 | 7/1964 | Davidson | 128/95.1 |
| 3,236,233 | 2/1966 | Thompson | 128/107.1 |
| 3,307,535 | 3/1967 | Locke | 602/19 |
| 3,393,675 | 7/1968 | Trznadel | 128/107.1 |
| 3,441,027 | 4/1969 | Lehman | 602/19 |
| 3,452,748 | 7/1969 | Caprio | 128/95.1 |
| 4,175,553 | 11/1979 | Rosenberg | 602/19 |
| 4,470,417 | 9/1984 | Gruber | 128/402 |
| 4,475,543 | 10/1984 | Brooks et al. | 602/19 |
| 4,556,055 | 12/1985 | Bonner | 128/402 |
| 4,702,235 | 10/1987 | Hong | 128/402 |
| 4,709,692 | 12/1987 | Kirschenberg et al. | 602/19 |
| 4,886,063 | 12/1989 | Crews | 128/403 |
| 5,007,412 | 4/1991 | DeWall | 602/19 |
| 5,062,414 | 11/1991 | Grim | 128/384 |
| 5,067,484 | 11/1991 | Hiemstra-Paez | 602/19 |

FOREIGN PATENT DOCUMENTS 586682 10/1933 Fed. Rep. of Germany ...... 128/384
2071 6/1984 PCT Int'l Appl. .................. 128/402

OTHER PUBLICATIONS

Omnipak, Advertisement by "Healthcare" Jun. 1982.

Primary Examiner—Mark Graham
Attorney, Agent, or Firm—Charles H. Thomas

[57] ABSTRACT

A lumbar support heating/cooling support belt is adapted to be worn over the lumbar spine and around the back of the user for back pain. The support has one pocket in the lower back section of the support. The pocket is capable of removably receiving a packet to create a thermal change in the pocket or provide air or foam rubber packets for support. There is an optional secondary support that runs over and attaches to the primary support. This provides additional desired muscular support by tightly or snugly adjusting via Velcro attachments around the back and sides. Then there are two criss-cross supports over the outer primary support which provide optional stiffness if desired by user. The two criss-cross supports both have an attached pocket which can house plastic or metal stays for even more support. This support provides the user many options and combinations in which to wear the support using all or some of the optional supports. The user also has the option to use one of various therapeutic devices at the same time. The wearer can use this support in any way or combination which best supports or controls his or her back pain.

13 Claims, 2 Drawing Sheets

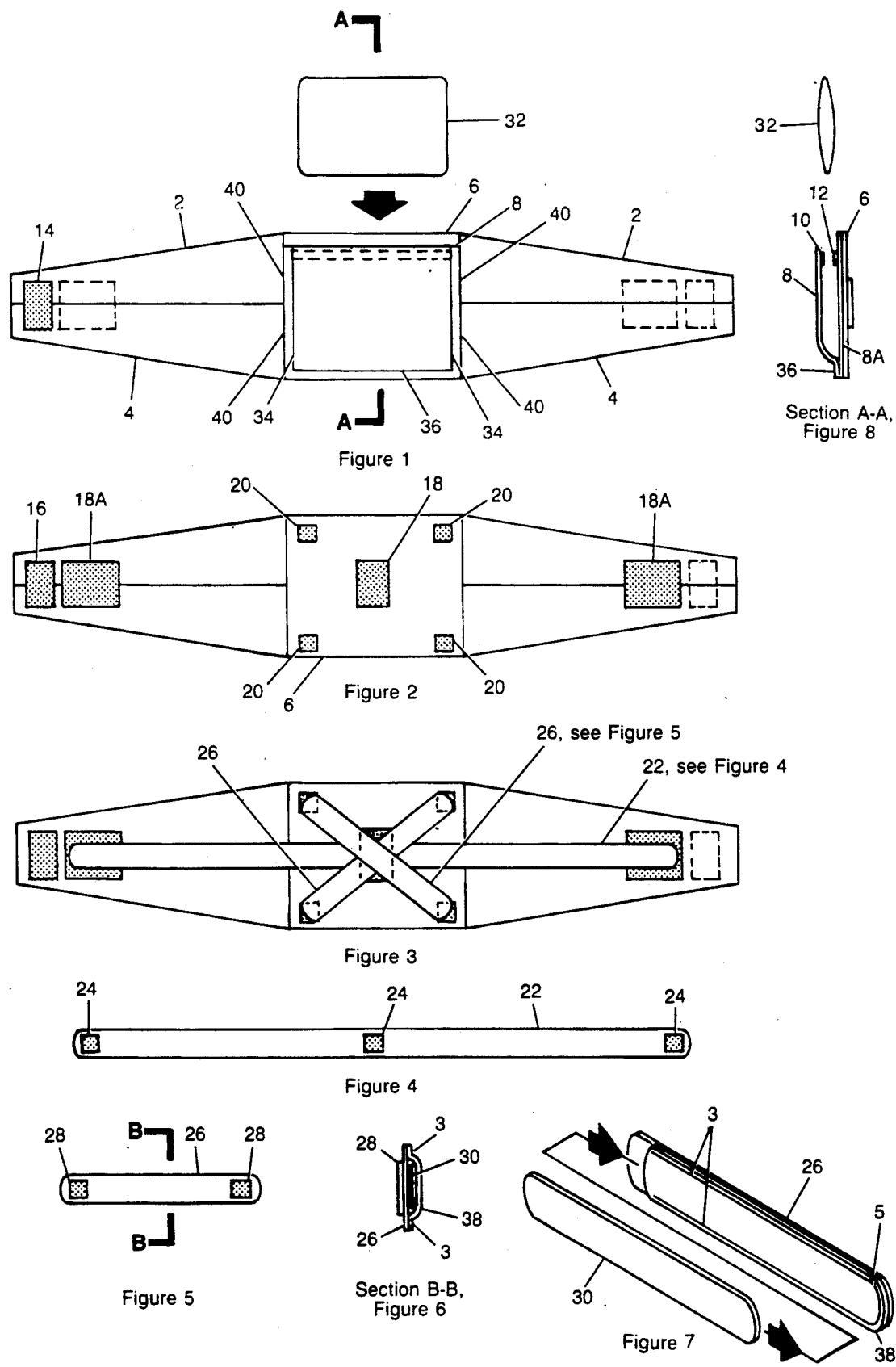

LUMBAR SUPPORT THERAPEUTIC HEAT/COOLING/AIR PILLOW BELT

BACKGROUND

The present invention is directed towards support of the lumbar spine and abdomen while at the same time having a built-in-pouch which is moisture resistant. The optional use of the pouch provides the therapeutic effects of locally applied heat, cold (cryotherapy), or an air pillow or foam rubber insert for seated postural support. This device is lightweight and made to be worn by humans while working in factories or working in an office.

Back pain due to injuries and/or congenital defects are the most common of debilitating conditions suffered by humans. It is well known that these conditions in the acute or chronic stage respond very well to certain kinds of lumbar support along with heat, cold and postural supports. However, most devices provide only support, though others may provide only cooling. It is the purpose of this invention to provide a multipurpose device which is light in weight, which provides primary and secondary support, and which provides three or more therapeutic options.

A variety of garments have been proposed for applying lumbar support. Some give limited therapeutic options but they all suffer from disadvantages. Devices designed to provide support and to provide optional therapeutic modalities are described in U.S. Pat. Nos. 4,556,055; 3,452,748; 3,013,561; 3,096,760; 4,886,063. Some of these garments are limited to support only, such as U.S. Pat. Nos. 3,013,561; 3,096,760; and 3,141,457.

U.S. Pat. Nos. 4,556,055 is a cold compress. It does not provide lumbar support or have an additional strap for added support.

U.S. Pat. No. 4,886,063 is also a therapeutic device. It is not meant to provide support for the lumbar spine. There are no straps, stays or options.

U.S. Pat. No. 3,452,748 is a back brace. It is very strong and non-flexible, but it is not light in weight. It is meant to immobilize and secure the spine, but it is very difficult to wear for someone who needs to work and have some mobility. It is designed to be used for immobility. The built-in back pad includes a supporting plate to include additional stiffness. There is no way this device can house therapeutic modalities while providing support. It is a brace, not a support. The device of the present invention is a support meant to protect while the user is working, sitting or playing. Also the device of U.S. 3,452,748 is not adaptable and the parts are not removable.

Accordingly, there is a need for a lumbar support that can be worn during daily activities and which also provides simultaneous therapeutic heat, cold or air support to the individual wearer. The device of the present invention meets this need. It is adapted to be worn over the lumbar spine for support, and provides therapeutic treatment of back pain. This lumbar support's particular purpose is to be used by people that may need one or more therapeutic modality, while simultaneously needing muscular support that is individually adjustable to the type of and amount of support desired.

SUMMARY

The lumbar support of the present invention meets this need. It is designed to be worn around the back, over the lumbar spine for muscular support and simutaneously provides therapeutic treatment of back pain. The support comprises an inner layer pouch pocket that is water resistant and capable of receiving a removable packet to either create a thermal change, i.e., cooling or heating, or it can provide support by receiving an air pouch or foam rubber pouch pad. The inner layer of material of the pocket is heat conductive so that the packet can alter the temperature of the lower back of the user of the garment.

The inner layer pouch pocket is attached to the primary lumbar support. The primary support compresses the pouch pocket firmly against the lumbar spine. This allows the thermally conductive packet to provide even contact on the back of the user. The compression contact is done by two pieces of woven elastic sewn on to each end of the elastic housing the pocket. These pieces of elastic comprise the primary support which wraps around the back, sides and abdomen of the user. The ends then join together over the abdomen compressing the therapeutic modality in the pouch pocket against the back of the user.

Preferably the pockets can either be heated or cooled depending upon whether the injury needs heating or cooling. Additionally if postural support is required while driving or being seated, the air pouch or foam rubber pad may be inserted into the pocket to provide the lumbar spine postural assistance. The pouch is flexible to accommdate variable amounts of air or foam rubber. This provides the individual the choice of, and amount of assistance needed.

The inner pouch pocket is impervious to water to avoid wetting the individual. Each pocket has a means of releasably closing the pocket such as a Velcro brand hook and loop fasteners. The inner layer pouch is sewn onto one piece of woven elastic making up the primary support.

The primary support is made up of multiple layers of woven elastic material sewn together in a particular manner. This allows the primary support a way of compressing the inner layer pouch packet modality firmly against the lumbar spine, while also acting as a primary lumbar support. The primary support has sewn onto it Velcro brand hook and loop fasteners. The Velcro fasteners allow the user attachment sites for additional lumbar supports. These additional supports allow the user to firm up and/or snug up the support to the desired pressure. Thus the user has the option of desired support or firmness needed to work, play or sit comfortably.

The secondary support has three Velcro attachment points that attach on complementing points on the primary support. One attachment point is on the center rear of both supports, and there are two other attachment points on each end of both supports. These sites provide attachment means for the secondary support to attach to the primary support. This provides the secondary support the means of firming and snugging over the primary support. The secondary support is adjustable over the primary support via the two end Velcro brand hook and loop fasteners.

There are also four Velcro attachment sites on the rear of the woven elastic center support. This is the reverse side of the woven elastic upon which the pouch pocket is sewn. These attachments are on each corner of the center support. They provide a means for contacting optional cross straps (called criss-cross attachments). These straps attach diagonally across the back in a criss-cross fashion and are attached also via Velcro brand hook and loop fasteners. They are placed in this sequence to provide additional firmness over the back of the wearer.

Additionally each criss-cross strap has built in pouch pockets. A plastic or metal stay may be inserted in the pouch pocket for optional support.

DESCRIPTION OF DRAWINGS

These and other features, aspects and advantages of the present invention will become better understood from the following description, appended claims, and accompanying drawing figures. I do not intend to limit this invention to particular details shown or described except as defined in the claims.

FIG. 1 is a front view of the side of the primary therapeutic support according to the present invention which faces the wearer. This figure show the pocket to house therapeutic modalities and woven elastic sewn onto both ends of the center support which comprises the primary support.

FIG. 2 is a rear view of the side of the primary therapeutic support opposite that of FIG. 1 showing features of the present invention. It shows Velcro attachments for the optional secondary support and criss-cross attachments.

FIG. 3 is a rear view showing the support of FIGS. 1 and 2 with an optional secondary support and criss-cross supports attached to Velcro fasteners of the primary support.

FIG. 4 is an isolated view of a secondary support showing Velcro attachment points.

FIG. 5 is an isolated view of one optional criss-cross attachment with Velcro attachment means.

FIG. 6 is a side section view taken along the lines B—B of FIG. 5 showing insertion of an optional plastic or metal stay.

FIG. 7 is a view showing how an optional stay is inserted into a pouch of one optional criss-cross strap.

FIG. 8 is a side sectional view taken along the lines A—A of FIG. 1 showing how a therapeutic packet is inserted and is secured in the pocket of the primary support.

REFERENCE NUMBERS IN DRAWINGS

2: WOVEN ELASTIC BAND SIDE SUPPORT UPPER PORTION
4: WOVEN ELASTIC BAND SIDE SUPPORT LOWER PORTION
6: WOVEN ELASTIC BAND CENTER SUPPORT WHERE POUCH POCKET ATTACHES
8: OUTSIDE LAYER POUCH MATERIAL
8A: INNER LAYER POUCH MATERIAL
10: VELCRO HOOK FASTENER ON CENTER CONNECTION FOR POUCH CLOSURE
12: VELCRO LOOP FASTENER ON POUCH CLOSURE
14: VELCRO LOOP FASTENER ON SIDE OF PRIMARY SUPPORT FOR CLOSURE OF THE PRIMARY SUPPORT
16: VELCRO HOOK FASTENER ON SIDE OF PRIMARY SUPPORT FOR CLOSURE OF THE PRIMARY SUPPORT
18: VELCRO HOOK FASTENER FOR CENTER ATTACHMENT OF SECONDARY OPTIONAL SUPPORT
18A: VELCRO HOOK FASTENER FOR SIDE ADJUSTMENT ATTACHMENTS OF SECONDARY OPTIONAL SUPPORT
20: VELCRO HOOK FASTENER ATTACHMENTS FOR DUAL CRISS-CROSS ATTACHMENTS
22: OPTIONAL SECONDARY SUPPORT
24: VELCRO LOOP FASTENERS ATTACHED TO SECONDARY SUPPORT
26: ONE OF TWO CRISS-CROSS DUAL ELASTIC SUPPORTS
28: VELCRO LOOP FASTENER ATTACHED TO CRISS-CROSS ATTACHMENTS
30: METAL OR PLASTIC STAY
32: PACKET THAT INSERTS IN POUCH POCKET OF PRIMARY SUPPORT
34: UPWARDLY EXTENDING STITCHED EDGE OF POUCH POCKET
36: STITCHED BOTTOM EDGE OF POUCH POCKET
38: CLOTH ATTACHED TO CRISS-CROSS ATTACHMENT TO COMPRISE POUCH FOR A METAL OR PLASTIC STAY
40: UPWARDLY STITCHED EDGE TO CONTACT WOVEN ELASTIC UPPER 2 AND LOWER 4 PORTION TO WOVEN ELASTIC 6
3: UPWARD STITCHED EDGE FOR CLOTH POUCH ON CRISS-CROSS ATTACHMENTS
5: BOTTOM STITCHED EDGE FOR CLOTH POUCH ON CRISS-CROSS ATTACHMENTS

DESCRIPTION FIG. 1-11

Figure 10:
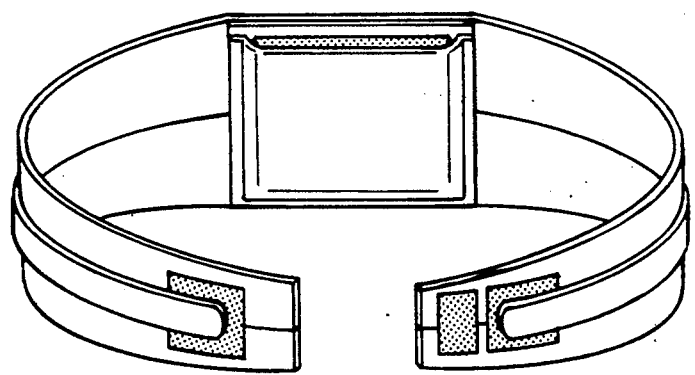
FIG. 10 is a perspective frontal view of the support showing the position it would assume when the end portions are drawn together and showing the secondary support attached to the primary support.
Figure 11:
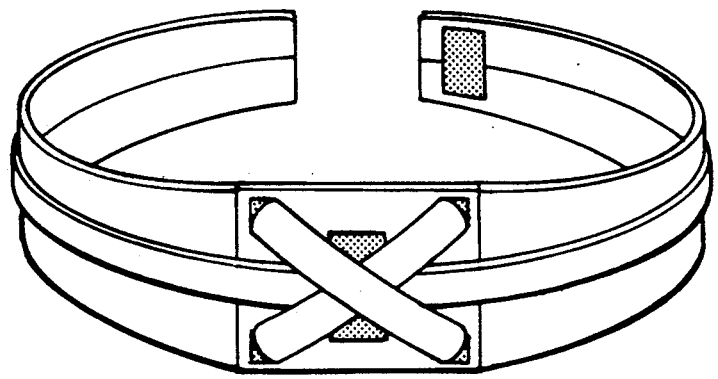
FIG. 11 is a perspective rear view of the lumbar support showing the position it would assume when the end portions are drawn together and showing two criss-cross straps attached on the primary support, and again showing the secondary support attached to the primary support.

Referring in detail to the drawings, the therapeutic lumbar support comprises, a therapeutic support sized to fit around the abdominal and lumbar regions of the wearers body such as shown in drawing FIGS. 10 and 11. A pouch pocket built into the primary support provides a means of placing different types of therapeutic modalities. The therapeutic lumber support provides many options also to the wearer. It can be worn with or without attached secondary support, or criss cross attachments. If criss cross attachment is used, a pouch for optional metal or plastic stays is built into it. Any one or all of these options can be worn together or seperately as desired by individual wearer for additional firmness or snugness. This support is designed to be worn under everyday clothing so it can be worn whatever the occasion.

The therapeutic lumbar support comprises an upper portion of woven elastic band 2 and a lower portion elastic band 4 stitched along edge 40 attached to woven elastic band 6. Woven elastic band 6 has attached to it pocket structure 8 and 8A. Stitched along upward edges 34 and bottom edge 36. This comprises the pouch pocket attached to woven elastic 6. The pouch pocket 8 and 8A has an upper portion also level and adjacent with woven elastic band 2 upper portion. The pouch pocket 8 and 8A have attached Velcro brand hook and loop attachments. Velcro hook fasteners 10 is attached to outside pouch pocket 8 and Velcro loop fastener 12 is attached to inner layer pouch 8A. This provides a means of removably opening and closing the pouch pocket to secure packet 32.

Figure 9:
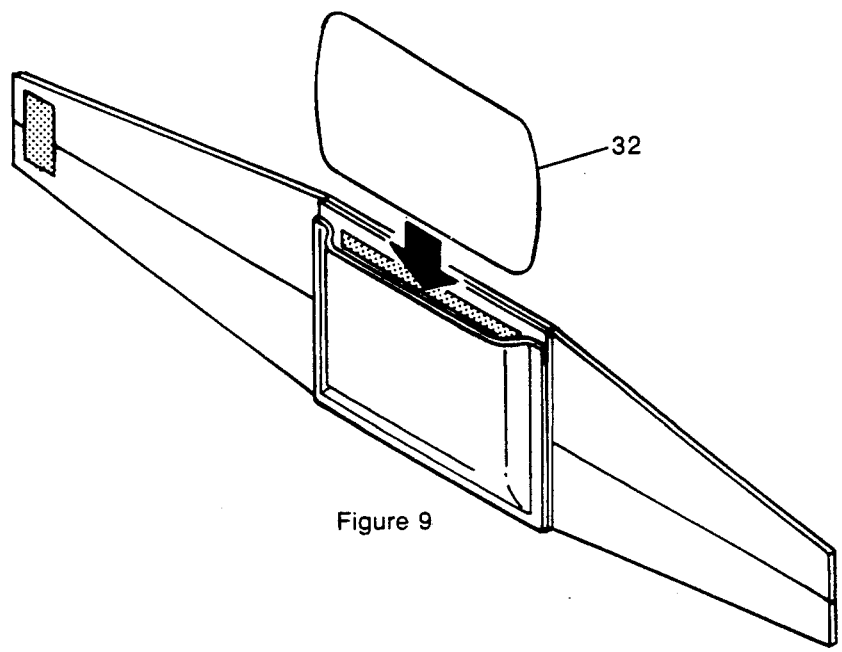
FIG. 9 is a front perspective view of the lumbar support showing one of the Velcro closures of the primary support and insertion of the packet into the pocket.

The pouch 8 is meant to be placed against the lower lumbar spine with therapeutic packet 32 inserted such as FIGS. 1, 9 and 10. After packet 32 is inserted and secured by way of Velcro hook and loop brand fastners 10 and 12. Both upper woven elastic band 2 and lower elastic band 4 have attached on opposite ends hook and loop fastners 14 and 16 as in FIG. 1 and FIG. 2. This allows both elastic brand ends of the primary support to encircle the body of the wearer and to engage each other via Velcro attachments 14 and 16. The Velcro attachments 14 and 16 allow the support to adjust on and over itself and support snugly around the wearer. This action also acts to compress pouch pocket 8 with packet 32 inserted evenly to provide either uniformly distributed heat, cold or support across the back of the user.

The pocket is self contained, being formed from a single piece of material, folded over to form an inner layer 8 and an outer layer 8A. The pocket is rectangular and is stitched to the woven elastic fabric 6 along the bottom edge 36 and upwardly extending up side edges 34.

The woven elastic band 6 to which the pouch pocket 8 and 8A attaches needs to be sufficiently strong to accomodate the weight of the packet 36. Additionally, the pouch pocket 8 and 8A is made of water impervious or resistant material such as a synthetic fiber so that when a cooling packet is used, moisture that condenses on the cooling pocket does not soak through the pocket and become an annoyance to the wearer. A suitable material is SUPPLEX (trademark) water resistant material.

The packet 32 can be of a type that provides cooling, provides heating or provides support to the lumbar spine depending on the treatment desired. A suitable cooling packet is of the type that is available for sports injuries. Even when the packet is cooled in the freezer, it remains flexible. Such a packet is available under the trademark Protem C. P. from Meyer Distributing Co., Inc. of Upland, Calif. It is cooled to the desired temperature merely by placing it in a freezer of a home refrigerator. A suitable packet that can be either heated or cooled is one from Jack Frost Laboratories, Incorporated of Fort Pierce, Fla. under catalog number 0737 as described in U.S. Pat. No. 4,756,311. These packets can be cooled by placement in a freezer, or alternatively can be heated to provide heat therapy by placing and heating them in a microwave oven. The other option is that the pocket 8, 8A can house a plastic inflatable air bag which can fit in the pocket to give the wearer lumbar support. This is especially useful for people who sit for long hours in a chair, car or truck, thus giving the wearer low back support in a sitting position. This air bag will be either custom made or we will continue to look for a similar device already manufactured. We have been unable to locate a similar type of device, so far, that will fit into the rectangular pouch along the small of the wearer's back. Also, a foam rubber insert packet may be provided to fit into pocket 8 and 8a cut in a rectangular manner so as to fit into the pouch and also provide support.

As shown in the rear view of FIG. 2 the primary support is sewn or glued onto the center woven elastic band 6 and Velcro hook fastener strip 18. A complementary Velcro loop fastener 24 in the middle of secondary support 22 attaches to Velcro hook fastner 18. This provides centeral attachment of the secondary support to the primary support. After the primary and secondary supports are attached, each end of the secondary support 22 wraps around the back, and around both sides of the user. Velcro loop fasteners 24 on each end of the secondary support then attach to complementary Velcro hook fasteners 18A sewn onto each end of the primary support on the upper and lower side supports 2 and 4, respectively. Velcro hook fasteners 18A are approximately 6" long and provide a means for the Velcro end loop fasteners of secondary support 22 to adjust by sliding along and attaching to Velcro hook fasteners 18A at any point desired as in FIG. 3. This provides user additional lumbar support over the primary support across the back. Which is adjustable to the user's taste.

FIG. 2 also shows 4 strips of Velcro brand hook fasteners 20, attached to each corner on the rear of woven elastic band 6 by glue or stitch. Velcro brand hook fasteners 20 allow two criss-cross attachment 26 to attach to their complementary Velcro loop fasteners 28. This provides a means of securing criss-cross attachment onto primary support. This gives the user the option of additional firmness across the small of the back if desired as in FIG. 3 and FIG. 11.

The material used to make up the criss-cross attachments 26 in this description is the same woven elastic as used throughout the support. Other materials can be used to make up the criss-cross supports such as leather or heavy woven cotton if desired.

Criss-cross attachments 26 shown in a sectional view BB of FIG. 6 shows that a pouch pocket 38 is capable of holding plastic or metal stay 30 which can be inserted as shown in FIG. 7. This is another option that this therapeutic support provides the wearers. The cross support can be worn with or without stays depending on the user's preference.

The pouch 38 as shown in FIG. 6 is one piece of fabric stitched to strap 26 along side edges 3 and along the bottom edge 5, as in FIGS. 6 and FIG. 7. This allows metal or plastic stay 30 to be inserted if desired.

This therapeutic support, according to the present invention, has significant advantages. It is light weight and can easily be worn under other garments. It allows the user to have a desired therapy throughout the working day and during physical activity, while at the same time providing the user many combinations of removable and attachable options for desired support and firmness.

Although the present invention has been described in considerable detail with reference to certain version thereof, other versions are possible. For example optional pouch pocket 8 and 8A may attach directly to woven elastic 2 (upper support) and woven elastic 4 (lower support) along stitch 40 without being sewn to woven elastic 6 and criss-cross Velcro hook fasteners 20 can attach to woven elastic 2 (upper support) or woven elastic band 4 (lower support) not to pouch 8 or 8A, giving cross supports longer range across the small of the back. Another version is that elastic upper band 2 and elastic lower band 4 can be made with one piece of elastic instead of two piece as the desired art has shown. In this one piece design elastic can be sewn either directly to optional pouch pockets 8 and 8A or to woven elastic band 6. The scope of appended claims should not be limited to the description of preferred versions contained herein.

What is claimed is:

1. A lumbar support adapted for wear on the human back for support thereof and for therapeutic treatment of back pain comprising:
   a primary support for positioning at the center of the lower back of a wearer and having inner and outer surfaces,
   secondary support attachment means and criss-cross support attachment means on said outer surface of said primary support
   elastic band means extending from opposition sides of said primary support for encircling the abdomen of a wearer, and having releasable mutually engageable end fastening means thereon and releasably engageable secondary support fastening means thereon,
   a pocket mounted on said inner surface of said primary support and adapted to receive a packet removably insertable into said pocket for selectively and alternatively creating a thermal change and for providing cushioning support,
   an elongated transverse secondary support disposed against said outer surface of said primary support and releasably secured thereto by said secondary support attachment means thereon and releasably secured to said elastic band means at said secondary support fastening means thereon,
   a pair of small straps releasably securable relative to each other in a criss-cross orientation against said outer surface of said primary support by said criss-cross support attachment means thereon, said small straps defining therewithin at least one pouch means, and
   stiff stay means removably insertable into said pouch means of said small straps.

2. A lumbar support according to claim 1 further comprising a packet, disposed in said pocket.

3. A lumbar support according to claim 2 wherein said packet is adapted to be heated to a temperature higher than body temperature and alternatively cooled to a temperature lower than body temperature.

4. A lumbar support according to claim 2 wherein said packet is adapted to hold air to provide lumbar support.

5. A lumbar support according to claim 2 wherein said packet contains foam rubber pad to provide lumbar support.

6. The support according to claim 2 wherein said pocket is impervious to water.

7. A lumbar support according to claim 1 wherein said end fastening means of said elastic band means are contact engageable fasteners that overlap each other to a selectively adjustable extent, whereby said elastic band means encircles and is adjustable to the girth of the body of a wearer.

8. A lumbar support according to claim 1 further comprising a packet disposed in said pocket and said elastic band means has sufficient elasticity to compress said packet firmly over the back of a wearer to apply pressure through said packet evenly across said back of said wearer.

9. A lumbar support according to claim 1 further comprising a packet disposed in said pocket and including means for releasably closing said pocket to encapsulate said packet therewithin.

10. A lumbar support according to claim 1 wherein said secondary support attachment means on said elastic band means are contact fasteners and said elongated transverse secondary support has mating contact fasteners thereon which are adapted to overlap said contact fasteners of said secondary support attachment means to a selectively variable extent, whereby tension on said elongated transverse secondary support means is adjustable to provide a desired level of comfort for a wearer.

11. A lumbar support according to claim 1 wherein said small straps each contain a pouch means to accommodate stiff stay means to provide additional stiffness across the back of a wearer.

12. A lumbar support according to claim 11 wherein said stiff stay means are fabricated of metal.

13. A lumbar support according to claim 11 wherein said stiff stay means are fabricated of plastic.

* * * * *